United States Patent [19]

O'Brien et al.

[11] 4,304,865

[45] Dec. 8, 1981

[54] HARVESTING MATERIAL FROM MICRO-CULTURE PLATES

[75] Inventors: Jacqueline A. O'Brien, Chandlers Cross; Stella C. Knight, Abbots Langley; Adam S. Platt, Bushey Heath; Noel A. Quick, Greenford, all of England

[73] Assignee: National Research Development Corporation, London, England

[21] Appl. No.: 68,338

[22] Filed: Aug. 21, 1979

[30] Foreign Application Priority Data

Aug. 31, 1978 [GB] United Kingdom ............. 35214/78

[51] Int. Cl.$^3$ .................. C12N 5/00; C12M 3/04
[52] U.S. Cl. .................. 435/240; 422/101; 422/102; 422/104; 435/261; 435/285; 435/310; 435/809
[58] Field of Search ............ 422/99, 101, 102, 104; 435/240, 241, 284, 285, 287, 299, 300, 301, 310, 809, 260, 261

[56] References Cited

U.S. PATENT DOCUMENTS

| 3,554,704 | 1/1971 | Ushakoff | 422/102 |
|---|---|---|---|
| 3,888,770 | 6/1975 | Avital et al. | 422/101 |
| 3,956,125 | 5/1976 | Strutt et al. | 422/101 |
| 3,990,852 | 11/1976 | Piazzi et al. | 422/102 |
| 4,090,850 | 5/1978 | Chen et al. | 23/230 B |
| 4,111,754 | 9/1978 | Park | 435/310 |
| 4,146,365 | 3/1979 | Kay et al. | 435/310 |

FOREIGN PATENT DOCUMENTS

| 806928 | 1/1959 | United Kingdom . |
|---|---|---|
| 1161792 | 8/1969 | United Kingdom . |
| 1187272 | 4/1970 | United Kingdom . |
| 1270745 | 4/1972 | United Kingdom . |
| 1310245 | 3/1973 | United Kingdom . |
| 1490362 | 11/1977 | United Kingdom . |
| 2005409 | 4/1979 | United Kingdom . |

Primary Examiner—Peter A. Hruskoci
Attorney, Agent, or Firm—Oblon, Fisher, Spivak, McClelland & Maier

[57] ABSTRACT

Apparatus for harvesting material from micro-culture plates comprises either a harvester plate or, in combination a harvester plate and a micro-culture plate, the harvester plate having a plurality of wells recessed into one surface thereof, these wells conforming in size, number and arrangement to the wells of the micro-culture plate, and the wells of the harvester plate being adapted to hold filter elements for absorbing liquid from corresponding wells of the culture plate when the wells of the culture plate, with the culture plate in an upside-down orientation, are contacted with corresponding wells of the harvester plate, and in which the harvester plate wells have fluid outlets at their bases. Also a new micro-culture plate comprises a plurality of wells recessed into a surface thereof each well comprising a fluid inlet passageway through the base thereof. Additionally a new method of harvesting material from a micro-culture plate comprises harvesting material from the wells of the micro-culture plate when the plate is maintained in an upside-down orientation, the material being transferred directly to absorbent elements such as filter paper discs.

8 Claims, 5 Drawing Figures

HARVESTING MATERIAL FROM MICRO-CULTURE PLATES

This invention relates to the harvesting of material, in particular cells, from micro-culture plates.

Micro-culture plates are widely used in hospitals and biological research laboratories for tests which involve the culturing or incubation of pluralities of samples, and allow for convenient miniaturisation of the quantities of sample and reagent used. Such micro-culture plates are customarily in the form of a plate, normally moulded from a plastics material, having a regularly spaced array of wells for holding separate samples recessed into a surface of the plate. At present, two types of micro-culture plate are commercially available: the Micro-Titre plate which is approximately $3\frac{1}{2}'' \times 5''$ in area having 12 rows of 8 wells each, the wells being about 3/16" in diameter and about $\frac{3}{8}''$ in depth, or the smaller scale Terasaki plate which is about $2\frac{1}{8}'' \times 3\frac{1}{8}''$ in area and has 10 rows of 6 wells each, the wells being about 1/16" in depth and tapering from diameters of about 5/32" at their mouths to about 1/32" at their bases.

Subsequent to incubation of samples in the wells of the microculture plate, material is typically harvested from the wells for monitoring or further processing as required. For example, in lymphocyte culture studies lymphocyte cell samples are cultured in the wells of a culture plate, cells are radioactively labelled and subsequently harvested, and the harvested cells are assayed by a radioactive counting technique. In the past the cells or other material have been harvested from the wells of the culture plate by tedious manual techniques involving a number of separate pipetting operations in which cell suspension and wash fluid are pipetted to and from each well in turn. Recently cell harvester apparatus has been developed to mechanise the harvesting procedure, and normally comprises a manifold having a plurality of groups of inlet and outlet tubes conforming to the arrangement of wells for removing cell suspension and adding and removing wash fluids etc. Such cell harvester apparatus, however, is complex and costly and is also prone to blockage by the cell suspensions. Moreover, in view of the smaller scale of Terasaki plates, the development of such harvester apparatus for these plates has not yet proved fruitful, and hitherto harvesting of cells from Terasaki plates has continued to be carried out manually.

Very recently a proposal has been put forward to culture cells in Terasaki plates which are maintained in an upside-down orientation, this having the advantages that cells tend to congregate at the meniscus of the cell culture droplet and do not adhere to the walls of the wells and also the cells are subjected to more efficient gassing than would be the case if the culture plate were right-way-up. In this recent proposal cells are harvested from the plate by conventional techniques, the culture plates being turned right-way-up before addition of the radioactive labelling reagent and before harvesting. A new method and apparatus for harvesting cells from micro-culture plates has now been developed which takes full advantage of the upside-down culturing technique.

Accordingly the present invention comprises a method of harvesting material from the wells of a micro-culture plate, in which sample material is harvested from the wells of the micro-culture plate whilst the plate is maintained in an upside-down orientation, the material being transferred directly from the wells of the culture plate to absorbent elements, such as filter paper discs.

Typically the material is harvested from the wells of the culture plate with the aid of capillary action, the mouths of the upside-down wells being brought into contact with absorbent elements, such as filter paper discs, which then absorb liquid containing the desired material e.g. cells, from the wells. It will be appreciated that if the method depends upon such capillary action it is necessary to ensure that the filter elements come into contact with the menisci of the sample droplets; for instance, the volumes of the samples being adjusted such that the menisci of the sample droplets are located approximately at or hang below the mouths of the wells.

The invention also provides new apparatus comprising, in combination, a micro-culture plate and a harvester plate, the harvester plate having a plurality of wells recessed into one surface thereof, these wells conforming in size, number and arrangement to the wells of the micro-culture plate, and adapted to hold filter elements for absorbing liquid from corresponding wells of the culture plate when the wells of the culture plate, with the culture plate in an upside-down orientation, are contacted with corresponding wells of the harvester plate, and in which the harvester plate wells have fluid outlets at their bases.

The invention also includes a harvester plate for use in the harvesting of material from the wells of upside-down micro-culture plates comprising a plate having a plurality of wells recessed into a surface thereof, the arrangement, size and number of wells conforming to that of a corresponding micro-culture plate, the wells adapted to hold filter elements for absorbing liquid, containing sample, from the wells of said corresponding micro-culture plate when the wells of the micro-culture plate, with the plate in an upside-down orientation, are contacted with corresponding wells of the harvester plate, and in which the harvester plate wells have fluid outlets in their bases.

The method and apparatus of the invention may be used for harvesting materials in general, usually solid particulate materials, from micro-culture plates, including absorbent or biologically treated beads or other particles, such as those which are commonly used in biological techniques, e.g. Sepharose or Sephadex beads. Normally, however, it is envisaged that the invention will be utilised for harvesting cells, such as lymphocyte cells and similar cells which are typically cultured during standard biochemical or clinical tests. The culture plates which may be harvested may be of any suitable size, shape or arrangement, provided they are capable of containing culture media during growth or incubation whilst in an upside-down orientation. In particular, the invention is applicable to harvesting from Terasaki plates, but also from Micro-Titre plates. It may be necessary, however, to modify the normal form of Micro-Titre plate to make it more satisfactory for use in the upside-down culturing and harvesting method. For instance, it may be desirable to provide a raised rim round the mouth of each well, such as is already provided as a "mode of construction" feature in Terasaki plates, to advantageously diminish the risk of samples from adjacent wells flowing into one another. Generally also, it is believed that the invention is applicable to harvesting from micro-culture plates having wells of sizes other than those of Terasaki and Micro- Titre plates, though such wells would not normally be greater than about ¼" in diameter. Furthermore, it is envisaged that new forms of culture plate and modified forms of existing culture plates, such as hereinafter described, may be developed specifically for use in the upside-down culturing and harvesting techniques, and such new and modified culture plates are also included within the scope of the present invention.

In preferred embodiments, the apparatus of the invention comprises means for cutting discrete discs of filter paper from a filter paper sheet to supply the filter elements required in the wells of the harvester plate. Particularly preferably the combined culture plate and harvester plate apparatus themselves together provide this means for cutting the discrete filter paper discs; for instance, by interacting formations on the mouths of the culture plate wells and the mouths of the harvester plate wells. For example, in the case of the Terasaki plate, the mouths of the wells of the harvester plate are of such a size that they are a close fit for the rims around the mouths of the culture plate wells when the culture plate wells and harvester plate wells are brought into contact with one another, such that a sheet of filter paper placed on top of the harvester plate is cut when the two plates are brought together to provide a plurality of filter paper discs, one for each well of the harvester plate. A Micro-Titre plate which has been modified by provision of rims around the mouths of the wells may be used to cut out the filter paper discs in the same way. Thus in a preferred embodiment of the apparatus of the invention the mouths of the culture plate wells have raised rims and the wells of the harvester plate are of such a size that they are a close fit for the rims when the wells of the two plates are brought together and the rims of the culture plate wells enter the mouths of the harvester plate wells.

A clean culture plate may be used to cut out the discs in the above manner before contacting of the culture containing culture plate with the harvester plate. Alternatively filter paper disc cutting and harvesting of the wells may be carried out in a single operation, for instance, by bringing the culture plate, containing the cultures, down on to a layer of filter paper covering the corresponding harvester plate.

Transfer of cells from the wells of the culture plate to the filter paper discs may be assisted by application of suction to the outlets in the bases of the harvester plate wells. For example, the harvester plate may be integral with or adapted for attachment to a reservoir which is connected to a vacuum source e.g. a conventional laboratory water pump. Subsequent to transfer of cells from the wells of the culture plate to the filter discs, the filter discs are usually washed, for instance, to remove unwanted radioactive contamination prior to radioactive counting, and suction, as described above, may be used to assist in washing of the filter paper discs. Usually the micro-culture plate is removed prior to washing of the filter discs, but in a preferred embodiment the bases of the wells of the micro-culture plate are provided with fluid inlet passageways through the plate and wash fluid may be passed to the filter discs via these passages. Such a modified form of micro-culture plate, having passageways drilled through the plate at the base of each well is included within the invention, and these passageways may advantageously provide inlet means for introducing reagents, such as radioactive labelling reagents, as well as the culture media itself to the wells of the culture plate, whilst it is maintained in an upside-down orientation.

The invention includes preferred methods of incubating cultures in micro-culture plates, in which the culture plates are maintained in the upside-down orientation throughout the incubation procedure including during addition of reagents, such as radioactive labelling reagents. Addition of reagents to the cultures may be effected by way of inlet passageways provided through the bases of the wells of modified culture plates, or by any other appropriate means. For example, the upside-down culture plate is tilted slightly and reagents are introduced into each well in turn by expelling a drop of reagent from a syringe reservoir on to the outside of a syringe needle, and touching the drop to the meniscus of the culture droplet in the mouth of the well.

The invention is further described by way of illustration only in the following description and example which refer to the accompanying diagrams in which.

Figure 1:
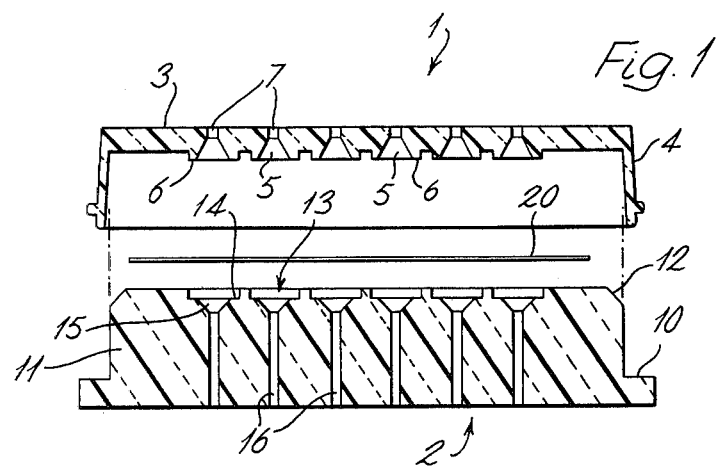
FIG. 1 shows, in enlarged scale, a vertical section end view through a combination modified Terasaki plate and harvester plate according to the invention.
Figure 2:
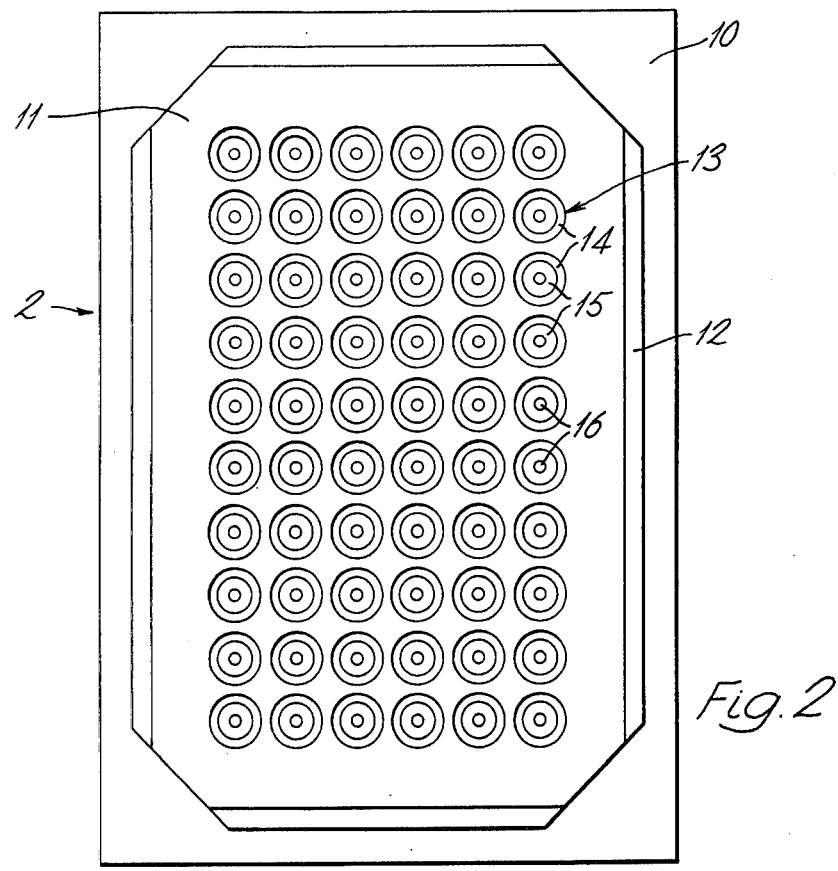
FIG. 2 shows a similar scale, plan view from above of the harvester plate of FIG. 1.

With reference to FIGS. 1 and 2 new apparatus according to the invention comprises a modified Terasaki plate 1 and a corresponding harvester plate 2.

The modified Terasaki plate is in the form of a conventional, commercially available Terasaki plate comprising a moulded plastic plate 2, of thickness about 2 mm and of area about 7.9×5.4 cms, having a wall section 4 of depth about 7 mm surrounding the surface of the plate 3 and extending therefrom at an angle slightly outwardly splayed from the perpendicular. The plate 3 has 10 rows of 6 conically shaped wells 5 recessed into its surface, each well 5 being about 3 mm in depth tapering from a diameter of about 4 mm at its mouth to about 1 mm at its base. The mouths of the wells 5 are raised above the surface level of plate 3 by sharp edged rims 6, of outer diameter about 5 mm and height about 1 mm. The plate 1 is modified with respect to the conventional, commercially available form of Terasaki plate by provision of fluid inlet passageways 7, of diameter about 1 mm, drilled through the plate 1 at the base of each well 5.

The corresponding harvester plate 2 comprises an oblong sheet 10 of polycarbonate plastic, of thickness about 3 mm and about 9.7×3.2 cms in area, having a raised oblong central portion 11, of thickness about 1.2 cms and about 7.9×5.4 cms in area, which is a tight push-fit into the volume enclosed by the wall 4 of plate 1. The corners of the central portion 11 have been machined away and a 1.5 mm chamfered edge 12 is provided around its top edges. 10 rows of 6 wells each 13, arranged so as to conform exactly to the arrangement of wells 5 of the modified Terasaki plate 1, are provided by recesses machined into the top surface of the portion 11. The wells 13 have cylindrical, sharp edged mouth sections 14, of depth about 0.5 mm and diameter about 5.3 mm and which are a tight push-fit for the rims 6 surrounding the wells 5 of plate 1. Below the mouth sections 14 the wells 13 have conical portions 15, of depth about 1.5 mm, which taper from a diameter of about 4 mm extending into passageways 16, of diameter about 1.2 mm, machined through the plate 2.

In use, cell cultures or other samples are incubated in the wells 5 of plate 1 which is maintained in the upside-down orientation, as in FIG. 1. The samples, and any reagents required during culturing, are introduced to the wells 5 through the passageways 7. Incubation is usually carried out in an enclosure, such as a plastic box with a loosely fitting lid, to prevent the cultures drying out, with saline solution disposed below the plate 1.

To harvest material from the wells 5, a sheet of filter paper 20 is placed over the top surface of the harvester plate 2 which is connected to a suction source, for instance, the plate 2 provides the top of an enclosed box (not shown) connected to a vacuum source e.g. a laboratory water pump. The plate 1 containing the sample droplets is then lowered on to the central portion 11 of plate 2 and the rims 6 of the wells 5 are pushed firmly home into the mouth sections 14 of the wells 13 of plate 2, the edges of which act as a dye cutting out sixty individual filter discs from the sheet of filter paper 20. Material originally contained in the wells 5 of plate 1 is transferred to filter discs held in the base of the wells 13. Alternatively the filter paper discs may be cut out previously using a clean dry plate 1 and the culture containing plate 1 lowered on to the plate 2 which already contains the filter paper discs. Suction may be applied to the wells 13 by way of the passageways 16 to assist transfer of material to the filter paper discs and also during subsequent washing procedures. It is normally necessary to ensure that the culture volumes of the wells 5 are between 15 and 23 µl so that the menisci of the culture droplets hang below the level of the rims 6 and material is successfully transferred directly from the wells 5 to the filter paper discs.

EXAMPLE

20 µl cultures containing different numbers of cells from a lymphoid cell line $CLA_4$, derived from human cord blood, were set up in triplicates in inverted, modified Terasaki plates 1 using a Hamilton Microlab P to set up doubling dilutions in 10% foetal calf serum in bicarbonate buffered Eagles medium.

Normal lymphocytes separated from defibrinated human peripheral blood using gelatin or ficoll triosil were suspended in bicarbonate buffered Dulbecco's medium with 15% autochthonous human serum gelatin. 20 µl triplicate cultures were set up as different cell concentrations using an Eppendorf pipette. Phytohaemagglutinin (PHA, Burroughs Wellcome, HA 15, 1 µl of a one in six dilution) was added to some cultures and the plates 1, inverted, were placed immediately above a bath of saline in a plastic box having a loosely fitting lid in an incubator gassed with 5% $CO_2$ in air. Tritiated thymidine (1 µl, 0.1 gm per well, specific activity 1 Ci/mM, Amersham, TRA 120 diluted with cold thymidine, Koch Light) was added to each culture, by way of the fluid inlet passageways 7, 24 hours before harvesting. Alternatively, for addition of thymidine to unmodified Terasaki plates, the plates are kept inverted but put in a holder at a slight angle, the thymidine solution (1 µl) is expelled from a Hamilton syringe on to the outside of the syringe needle and is then introduced into each culture by touching the thymidine droplet on to the meniscus of the culture.

Cells were harvested from the above cultures by the method described above. After transfer of the cells to the filter paper discs the filters were washed with saline, trichloroacetic acid (5%) and methanol added from a syringe; the plate 1 being either maintained over the plate 2 and the wash liquids introduced through the inlets 7, or the plate 1 being first removed and the wash fluids fed directly into the walls 13.

The dried filters were transferred to scintillant (NE 260, Nuclear Enterprises) using a hand-held hypodermic needle and counted in a liquid scintillation counter.

Figure 3:
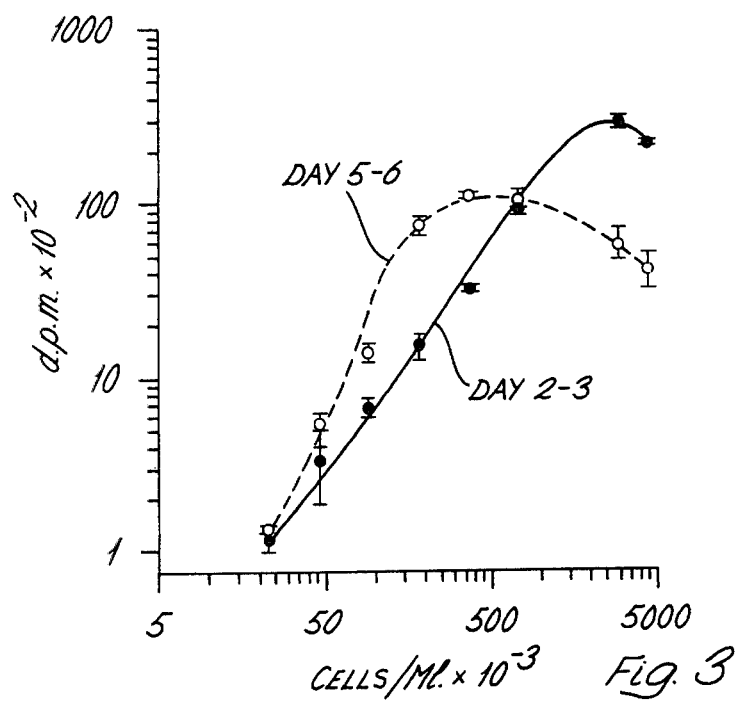
FIG. 3 shows a graph of results obtained after incubation and harvesting of cells using the method and apparatus of the invention.
Figure 4:
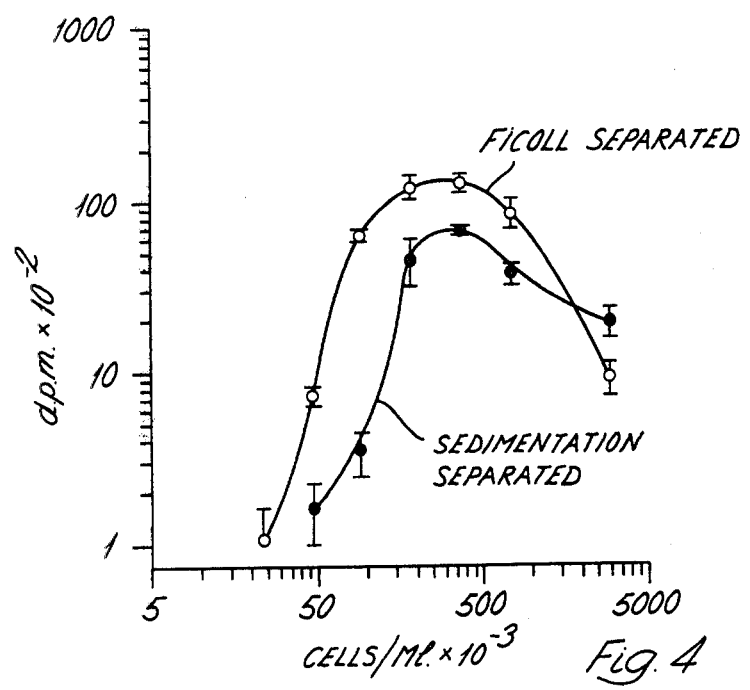
FIG. 4 shows a similar graph to that of FIG. 3.
Figure 5:
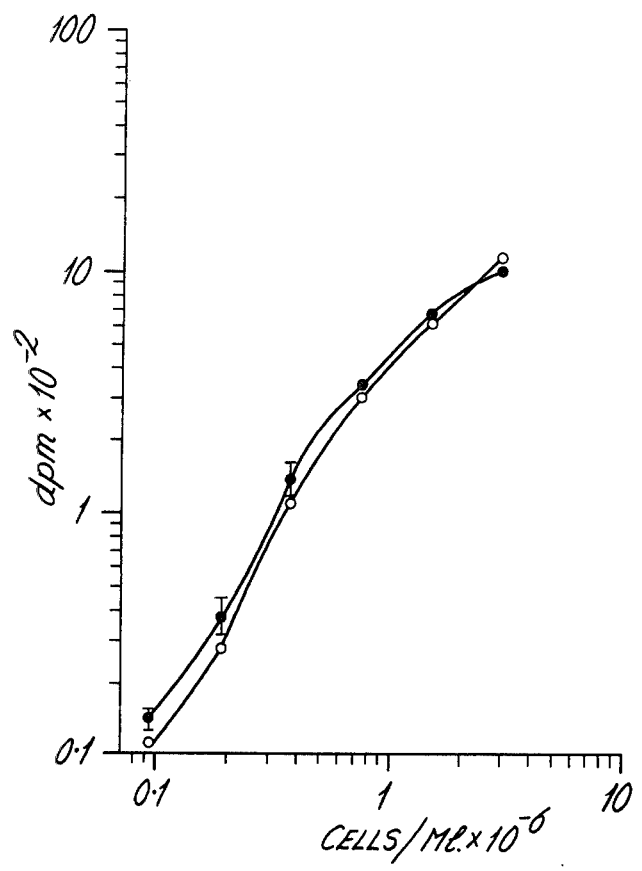
FIG. 5 shows a further similar graph relating two sets of results.

The results obtained are shown in FIGS. 3 and 4. FIG. 3 shows graphically the mean responses (dpm) obtained for triplicate cultures, with standard errors, for the uptake of $^3$H-thymidine into the acid precipitable fraction of gelatin-separated human lymphocytes stimulated with PHA in cultures containing different numbers of lymphocytes. The points •——• refer to day 2–3 and the points o - - - - o refer to day 5–6. Similarly FIG. 4 shows graphically the mean responses (dpm) from triplicate cultures, with standard errors, for the uptake of $^3$H-thymidine into the acid precipitable fraction of human lymphocytes cultured at different cell concentrations on the 6–7th day of culture with PHA; the points (o) referring to cells separated with ficoll and the points ( • ) referring to cells separated by sedimentation with gelatin. There was no evidence of any crossover of material between filters during harvesting e.g. 4 day cultures containing different numbers of PHA stimulated lymphocytes had 12,529, 10,358 and 5,214 dpm and on adjacent filters there were control, non-stimulated cells with counts of 28, 38 and 19 dpm respectively. Results were reproducible as demonstrated from the activity of different concentrations of CLA cells. The results obtained from two sets of triplicate cultures are similar and are shown in FIG. 5, which relates to the uptake of $^3$H-thymidine into the acid-precipitable fractions of cells during the first 24 hour period of culture with different concentrations of cells.

We claim:

1. Apparatus for harvesting material from microculture plates comprising, in combination, a micro-culture plate and a harvester plate, the harvester plate having a plurality of wells recessed into one surface thereof, these wells conforming in size, number, and arrangement to the wells of the micro-culture plate which are of a conical shape with the wider openings of said conically shaped wells on one side of said micro-culture plate being of a diameter less than about one quarter of an inch which is a size sufficient for culturing biological samples while the micro-culture plate is in an inverted position and the narrower openings of said conically shaped wells being in open communication with fluid inlet passages which are open to the other side of said micro-culture plate, said wells of said culture plate having raised rims about the same and the wells of said harvester plate being such a size that they are a close fit for the rims when the wells of the two plates are brought together and the rims of the culture plate wells enter the mouths of the harvester plate wells, and the wells of the harvester plate capable of holding filter elements by virtue of their shape for absorbing liquid from corresponding wells of the culture plate when the wells of the culture plate, with the culture plate in an upside-down orientation, are contacted with corresponding wells of the harvester plate, and in which the harvester plate wells have fluid outlets at their bases.

2. Apparatus according to claim 1 comprising means for cutting discrete discs of filter paper from a filter paper sheet to supply the filter elements required in the wells of the harvester plate.

3. Apparatus according to claim 2 in which the means for cutting discrete discs of filter paper is provided by contact of the mouths of the culture plate wells with the mouths of the harvester plate wells as the culture plate is mated with the harvester plate.

4. A method of culturing biological samples and harvesting the same, comprising: culturing biological liquid samples in a plurality of wells in a micro-culture plate while said micro-culture plate is in an inverted position, the wells in said micro-culture plate being of a conical shape with the wider openings of said conically shaped wells on one side of said microculture plate being of a diameter less than about one quarter of an inch and thus being sufficient for culturing said samples while said micro-culture plate is inverted, said wells having raised rims provided about the mouths of the same; mating said micro-culture plate after culturing with a harvester plate containing a plurality of wells recessed into one surface thereof, these wells conforming in size, number and arrangement to the wells of said micro-culture plate, being of such a size that they are a close fit for said rims when the wells of the micro-culture plate and the harvester plate are brought together and the rims of the culture plate wells enter the mouth of the harvester plate wells, and having fluid outlets at their bases and said harvester plate wells being capable of holding filter elements by virture of their shape for absorbing liquid from the corresponding wells in the culture plate; and filtering said samples in the wells of said micro-culture plate through said absorbent elements while the micro-culture plate is maintained in an inverted position.

5. The method of claim 4, wherein the absorbent elements are retained in the wells of the harvester plate.

6. The method of claim 5, in which transfer of cells from the wells of the culture plate to the filter paper discs is assisted by application of suction to the outlets in the bases of the harvester plate wells.

7. The method of claim 4, wherein in the mating of said harvester plate and said micro-culture plate, paper filter discs are cut out of a sheet of filter paper sandwiched between said plates, said filter discs being provided for each well of said harvester plate.

8. The method of claim 7, in which filter paper disc cutting and harvesting are carried out in a single operation by bringing the upside-down culture plate, containing the culture, down onto a layer of filter paper covering the wells of a corresponding harvester plate.

* * * * *